(12) United States Patent
Shelley et al.

(10) Patent No.: US 8,436,311 B2
(45) Date of Patent: May 7, 2013

(54) METHOD OF PREDICTING THERMAL OR CHEMICAL EFFECT IN A COATED OR PAINTED COMPOSITE MATERIAL

(75) Inventors: Paul H. Shelley, Lakewood, WA (US); Gregory J. Werner, Puyallup, WA (US); Paul G. Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 402 days.

(21) Appl. No.: 12/684,368

(22) Filed: Jan. 8, 2010

(65) Prior Publication Data

US 2011/0001047 A1    Jan. 6, 2011

Related U.S. Application Data

(63) Continuation-in-part of application No. 12/164,023, filed on Aug. 14, 2008.

(51) Int. Cl.
*G01J 5/02* (2006.01)
(52) U.S. Cl.
USPC .................. 250/341.8; 250/341.1; 250/340
(58) Field of Classification Search ............... 250/341.8, 250/341.1, 340
See application file for complete search history.

(56) References Cited

U.S. PATENT DOCUMENTS

| | | | |
|---|---|---|---|
| 5,638,284 A | 6/1997 | Helmer et al. | |
| 5,965,888 A | 10/1999 | Engstrom et al. | |
| 6,434,267 B1 * | 8/2002 | Smith | 382/162 |
| 6,784,431 B2 | 8/2004 | Shelley et al. | |
| 6,794,651 B2 | 9/2004 | Shelley et al. | |
| 6,903,339 B2 | 6/2005 | Shelley et al. | |
| 6,906,327 B2 | 6/2005 | Shelley et al. | |
| 7,115,869 B2 * | 10/2006 | Shelley et al. | 250/341.8 |
| 7,223,977 B2 | 5/2007 | Shelley et al. | |
| 2002/0107644 A1 | 8/2002 | Meglen et al. | |
| 2002/0113212 A1 | 8/2002 | Meglen et al. | |
| 2007/0131862 A1 | 6/2007 | Cowan et al. | |
| 2009/0321648 A1 | 12/2009 | Shelley et al. | |

FOREIGN PATENT DOCUMENTS

| | | |
|---|---|---|
| EP | 2138829 A1 | 12/2009 |
| EP | 2138830 A2 | 12/2009 |

OTHER PUBLICATIONS

Adamsons, K., Chemical surface characterization and depth profiling of automotive coating systems, 2000, Progress in Polymer Science, vol. 25, 1363-1409.*
Lemaire et al., Prediction of Coating Lifetime Based on FTIR Microspectrophotometric Analysis of Chemical Evolutions, Apr. 15, 1999, American Chemical Society, 246-256.*
Gerlock et al., On the use of Fourier transform infrared spectroscopy and ultraviolet spectroscopy to assess the weathering performance of isolated clearcoats from different chemical families,1998, Polymer Degradation and Stability, vol. 62, pp. 225-234.*
Extended Search Report for EP Application No. 1150399.1 dated Apr. 20, 2011.
Extended Search Report for EP Application No. 09251357.1 dated Oct. 9, 2009.

* cited by examiner

*Primary Examiner* — Christine Sung
(74) *Attorney, Agent, or Firm* — Parsons Behle & Latimer (57) ABSTRACT

A method of predicting thermal or chemical effect in a painted or coated composite material includes generating a calibration model, providing a composite material having a coating layer, irradiating the coating layer with infrared energy, detecting infrared energy reflected from the coating layer and predicting a thermal or chemical history of the coating layer using the calibration model and the infrared energy reflected from the coating layer.

21 Claims, 8 Drawing Sheets

METHOD OF PREDICTING THERMAL OR CHEMICAL EFFECT IN A COATED OR PAINTED COMPOSITE MATERIAL

CROSS REFERENCE TO RELATED APPLICATIONS

This application is a continuation-in-part of co-pending U.S. patent application Ser. No. 12/164,023 filed Aug. 14, 2008, which is related to co-pending U.S. patent application Ser. Nos. 12/164,025, 12/164,026, 12/164,022, and 12/164,017, all filed on Jun. 28, 2008, each of which applications is incorporated by reference herein in its entirety.

TECHNICAL FIELD

The disclosure relates to methods for determining thermal or chemical effect in composite materials. More particularly, the disclosure relates to a method for accurately assessing thermal or chemical effect in a coated or painted composite material using infrared spectroscopy.

BACKGROUND

Resin-fiber composite materials are utilized in a variety of applications including the aerospace industry, for example. Structures which are constructed of resin-fiber composite materials may be exposed to heat, which may affect the composite materials in various ways. These heat-induced effects may include chemical changes such as oxidation, material loss and the breaking and/or forming of chemical bonds occurs in the polymer chemical structure of the composite materials. Resin decomposition, strength effect, charring and fiber decomposition of the composite materials may occur at increasing temperatures.

Composite materials and epoxy-based surfacing films are typically cured under a vacuum at 250-350° F. for several hours. Repairs to the composite materials or surfacing films may be necessary after initial manufacturing. These repairs may require the use of heating blankets. Heat blankets may have hot spots. Thus, during the repair some areas of the composite material or surfacing film may become overheated; in the case of epoxy-based surfacing films, a color change (dark or blackened) may be noticeable. Thermal effect for in-service airplanes can occur from engine and run-way fires, electrical problems, lightning strikes, and other causes. Thermal effect may affect the mechanical and structural integrity of composite materials and surfacing films.

Repair or removal of heat-effected composite materials or surfacing films on a structure may involve first determining the degree of harmful heat effect to the composite materials or surfacing films. Although determining the degree of heat effect to composite materials or surfacing films may be performed by visual inspection, heat effect may not be visually apparent. Previous methods of determining the presence and extent of heat effect in composite materials and surfacing films includes obtaining an infrared spectrum of a heat-affected composite standard and correlating the infrared spectrum obtained from the composite standard with the degree of thermal effect of the composite standard. An infrared spectrum obtained from the composite material or surfacing film the heat effect of which is in question can then be compared to the infrared spectrum obtained from the composite standard to determine the presence and assess the degree of thermal effect in the composite material or surfacing film. Current methods of determining the presence and extent of heat effect in composite materials and surfacing films include obtaining the spectra of a series of heat-affected composite standards and building a multivariate model with the spectra of those standards. An infrared spectrum obtained from the composite material or surfacing film which is in question can then be predicted by the multivariate model to determine the presence and assess the degree of thermal effect in the composite material or surfacing film.

U.S. Pat. No. 7,115,869 discloses a method for measurement of composite heat effect with infrared spectroscopy by which an amount of heat exposure to a resin-fiber composite substrate is determined. According to the method, the intensity of infrared energy reflected by a composite substrate is determined at multiple wavelengths. The amount of infrared energy which is reflected or absorbed at these wavelengths is correlated to a degree or amount of heat exposure of the composite substrate. The thermal effect measurement method of the present disclosure is more sensitive than that which is disclosed in U.S. Pat. No. 7,115,869 and is richer in spectral detail, providing a better indication of whether thermal effect has occurred in a composite material as well as the extent of effect. Moreover, the method can be implemented using a hand-held spectrometer which facilitates convenience and flexibility in measuring the possibility or degree of thermal effect in the composite material in question.

Calibration of infrared spectrometers to residual strength in composite materials or surfacing films correlates the resin condition as read from the infrared spectrum to the residual strength of the material or film which degrades as the resin degrades with progressively increasing temperatures. Therefore, the infrared sensors may be calibrated using time-controlled thermal soak standards which are obtained by exposing various composite materials or surfacing film controls to various temperatures for a particular time period such as one hour, for example. One method of preparing the standards includes placing the standards in an oven which is calibrated periodically and monitored continuously using multiple thermocouples as the composite materials are thermally exposed. Furthermore, thermal effect to composite materials or surfacing films may not follow a linear course. The most useful parameters for thermal effect are those that the repair process person can understand and use as criteria for removal of effect material. Under circumstances in which it is desirable to remove all weakened material, a measure of the residual strength in the material is best. Multivariate calibration allows calibration to such physical properties under circumstances in which previous calibration methods were insufficient.

Infrared spectroscopy is a promising technique for non-destructive inspection of composites. Conventional inspection of coated or painted composites may require that the coating or paint be removed from the composite to facilitate direct analysis of the composite. The sampling interfaces available for infrared spectrometers may be negatively impacted by changes in the surface properties of paints and coatings. This method, however, may be time-consuming. Furthermore, due to uneven surfaces of composite materials, it may be difficult to completely remove the coating or paint from the composite. Because some coating or paint may remain on the composite, the degree of sample preparation may be highly subjective and may vary from person to person. Moreover, removal of coating or paint from the composite may involve chemical and/or physical processes that may damage the underlying composite.

Therefore, a method for accurately assessing thermal effect in a coated or painted composite material using infrared spectroscopy is needed.

SUMMARY

The disclosure is generally directed to a method of predicting thermal or chemical effect in a painted or coated composite material. An illustrative embodiment of the method may include generating a calibration model, providing a composite material having a coating layer, irradiating the coating layer with infrared energy, detecting infrared energy reflected from the coating layer and predicting a thermal or chemical history of the coating layer using the calibration model and the infrared energy reflected from the coating layer.

In some embodiments, the method may include generating a calibration model by calibrating infrared data to thermal or chemical effect information on painted or coated composite standards; providing a composite material having a coating layer; irradiating the coating layer with infrared energy; detecting infrared energy reflected from the coating layer; and predicting a thermal or chemical history of the coating layer using the calibration model and the infrared energy reflected from the coating layer.

In some embodiments, the method may include generating a calibration model by calibrating infrared data to thermal or chemical effect information on painted or coated composite standards; providing a composite material having a coating layer; irradiating the coating layer with mid-infrared energy; detecting infrared energy reflected from the coating layer; obtaining an infrared spectrum of the infrared energy reflected from the coating layer; and predicting a thermal or chemical history of the coating layer using the calibration model and the infrared energy reflected from the coating layer.

In some embodiments, the method may include generating a calibration model by providing composite standards having painted or coated surfaces; subjecting the painted or coated surfaces on the composite standards to varying degrees of heat intensity; irradiating the painted or coated surfaces on the composite standards with infrared energy; detecting the infrared energy reflected from the surfaces and obtaining infrared spectra of the infrared energy reflected from the surfaces; providing a composite material having a painted or coated layer; providing a hand-held spectrometer having a specular-reflectance and specular-diffuse-reflectance sampling interface; irradiating the layer with mid-infrared energy from the spectrometer; detecting infrared energy reflected from the layer with the spectrometer; obtaining a spectrum of the infrared energy reflected from the layer; and predicting a thermal history of the layer using the calibration model and the infrared energy reflected from the layer.

BRIEF DESCRIPTION OF THE ILLUSTRATIONS

DETAILED DESCRIPTION

Figure 1:
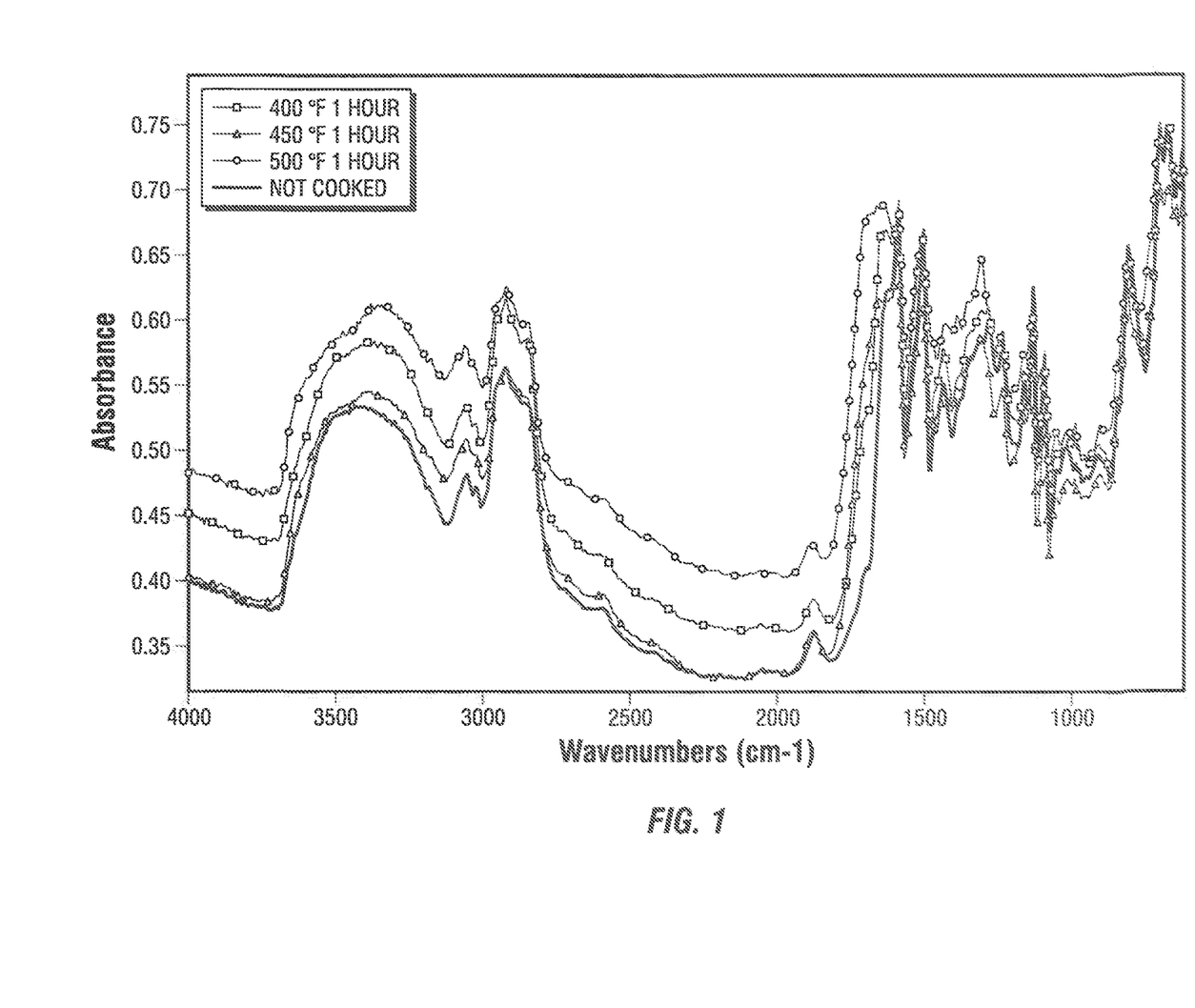
FIG. 1 is a series of mid-IR spectra on thermally exposed graphite composite (CFRP) standards which were exposed for 1 hour each at 400, 450 and 500° F. and no thermal exposure, respectively.
Figure 2:
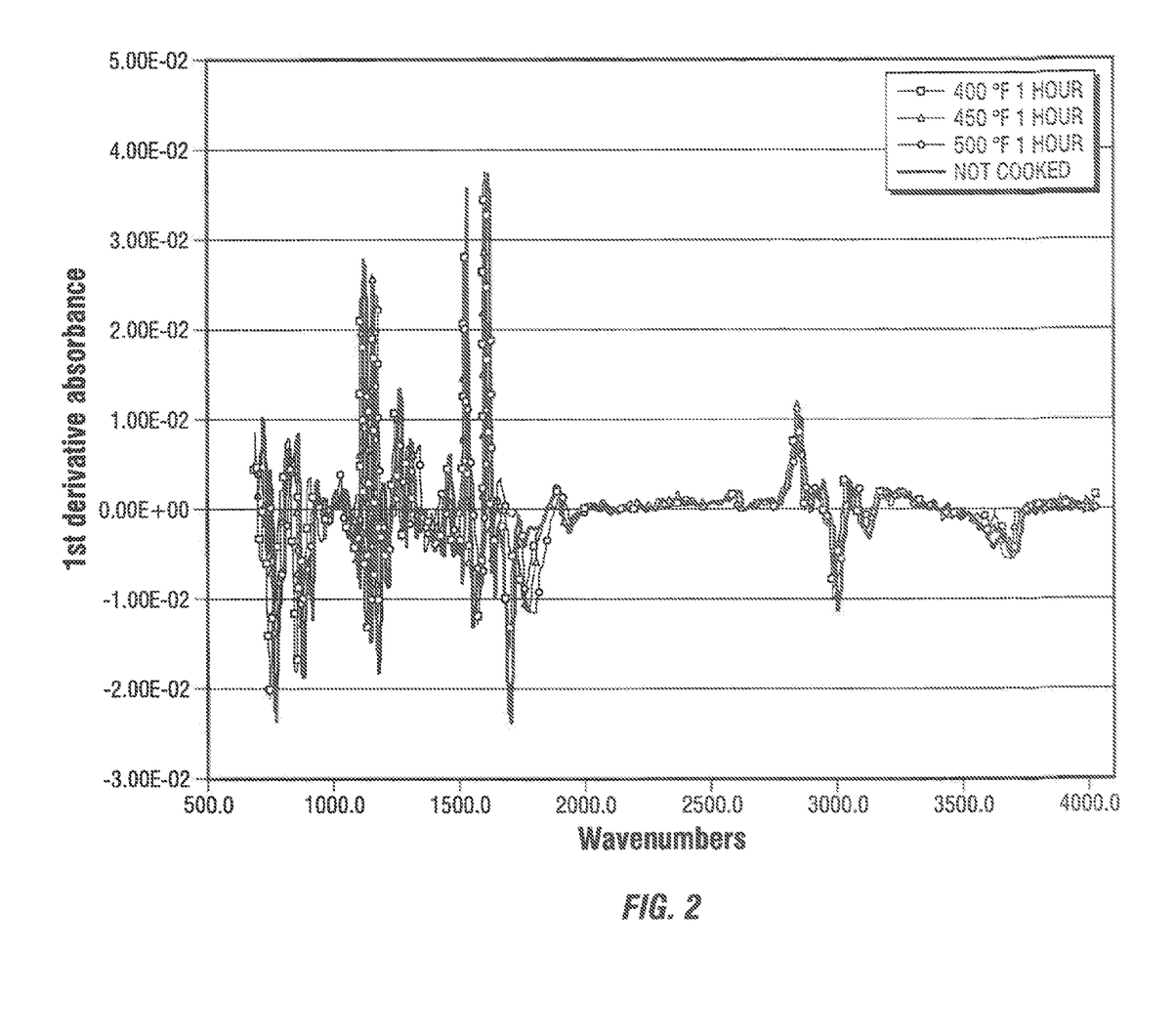
FIG. 2 is a the same series of mid-IR spectra from FIG. 1 but with first derivative and 7 point smoothing pre-processing with the Savitzky Golay method.

Referring initially to FIGS. 1-4, an illustrative embodiment of a method of multivariate calibration for thermal effect with mid-IR spectra is shown. As shown in block 402 of flow diagram 400 in FIG. 4, the thermal effect calibration begins with providing CFRP standards that are carefully heated using carefully-controlled thermal exposure devices in a range of interest and then tested to obtain residual mechanical properties data. Block 404 shows the mid-IR spectral data collection step in which infrared spectra may be collected on the standards with one or more spectra on each standard. In some applications, a hand-held spectrometer may be used to measure the spectral properties of the material in question. The raw infrared spectra obtained for the standards are shown in FIG. 1. Block 406 describes the data pre-processing step and FIG. 2 shows the results of a typical pre-processing method.

Figure 3:
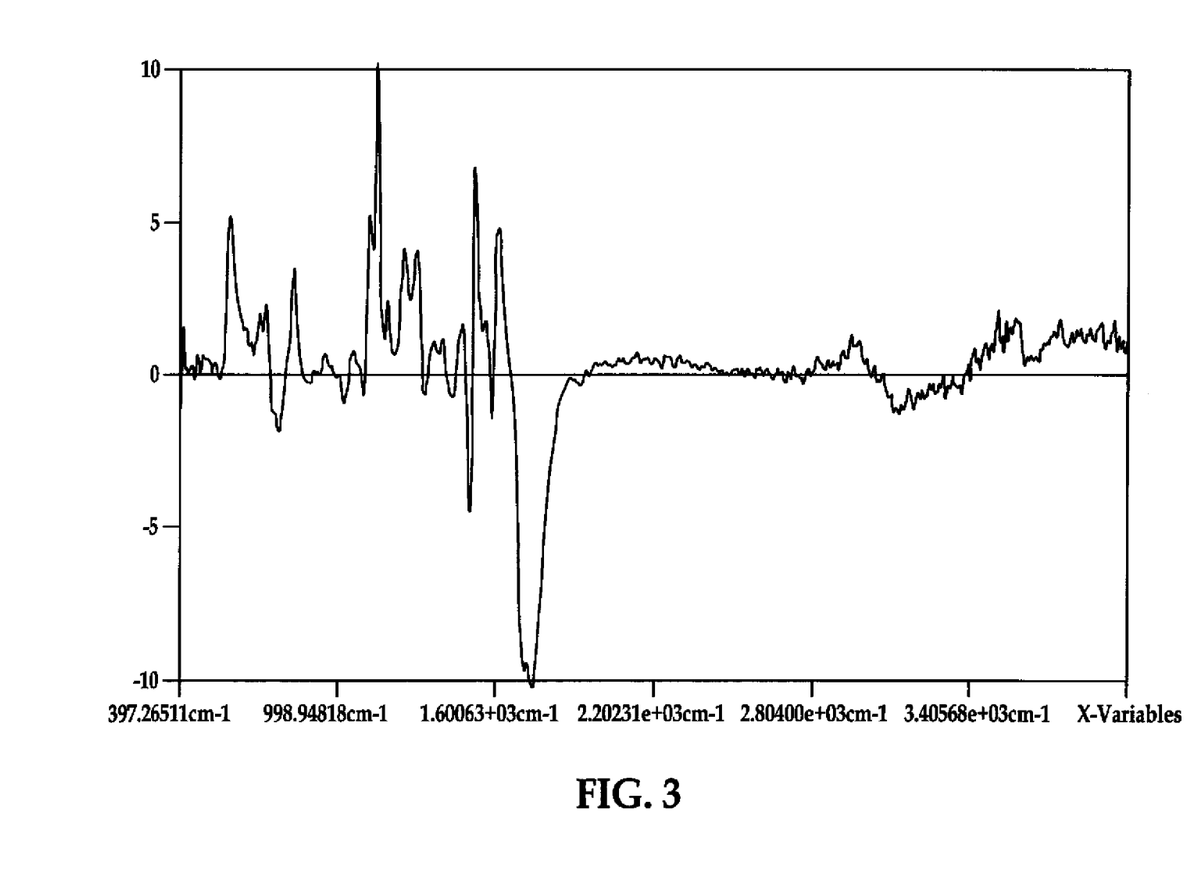
FIG. 3 is the regression vector (either Predicted Residual of the Estimated Sum of Squares or Standard Error of Cross-Validation) from a multivariate calibration of the mid-IR spectra to un-notched compression test stress results of the standards using the PLS (partial least squares) multivariate calibration method.

Block 408 shows the multivariate calibration step which may be carried out using a PLS routine or an alternative multivariate calibration method. Correlation of the infrared spectra to thermal exposure or mechanical properties data for a composite material is obtained. FIG. 3 shows the regression coefficients that result from that calibration. Block 410 shows the step where the multivariate calibration is saved in an appropriate format, converted into a method file and then loaded into the hand-held mid-IR device that will be used to read thermal effect on the CFRP material in question. In some embodiments, block 408 and block 410 may be replaced by collecting a single set of Validation Spectra that can be calculated by each new iteration of the calibration method. Ideally, these Validation Spectra may be collected on samples that are not included in the calibration set. Block 412 shows the CFRP material in question being predicted for residual stress values that would indicate the extent of thermal effect in the material in question using the new calibration model in the spectrometer method file. If the original standards are predicted here, an accuracy figure for the methods can be obtained based on the difference between the known stress numbers and those predicted by the method just developed.

Figure 4:
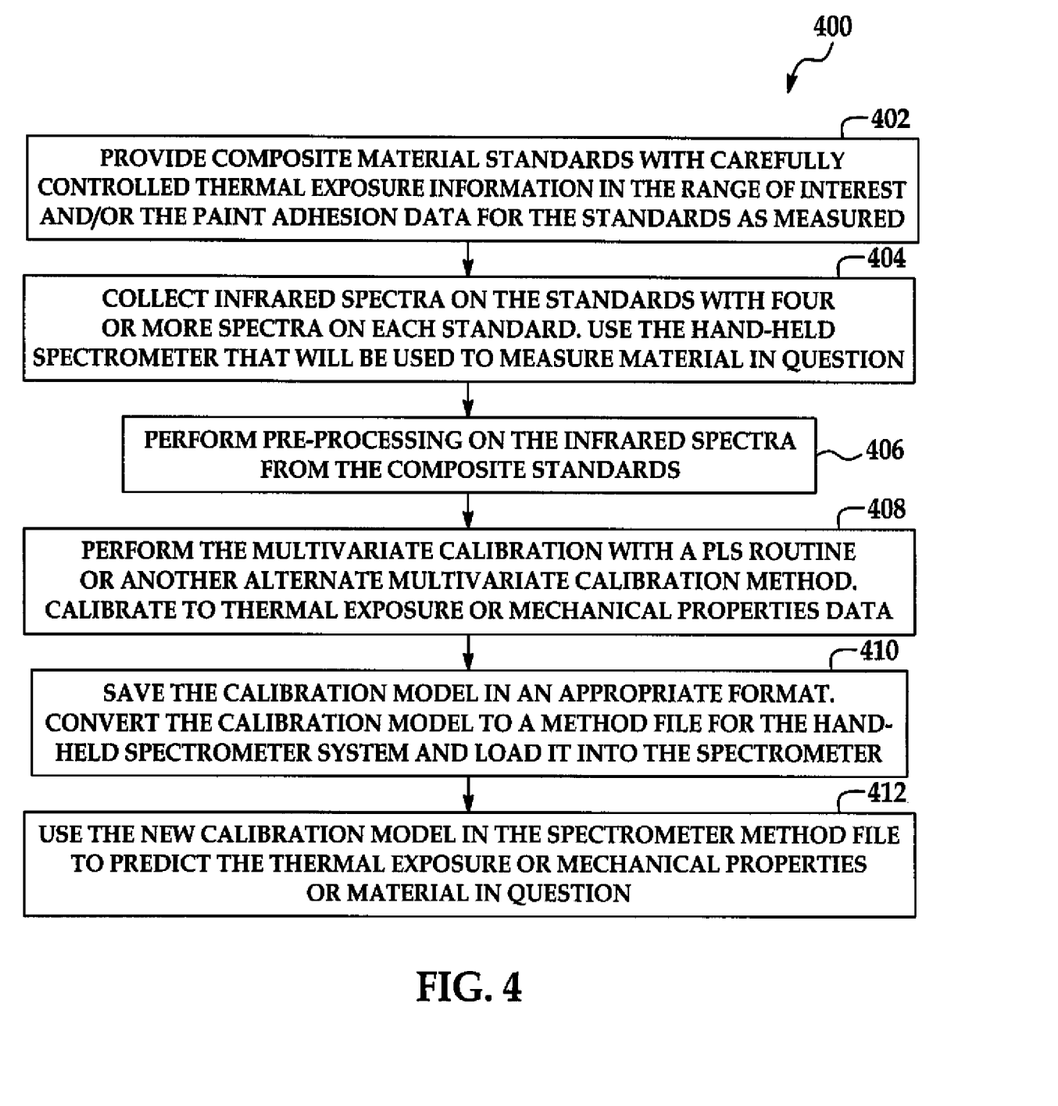
FIG. 4 is a flow diagram which illustrates the multivariate calibration and prediction method.
Figure 4A:
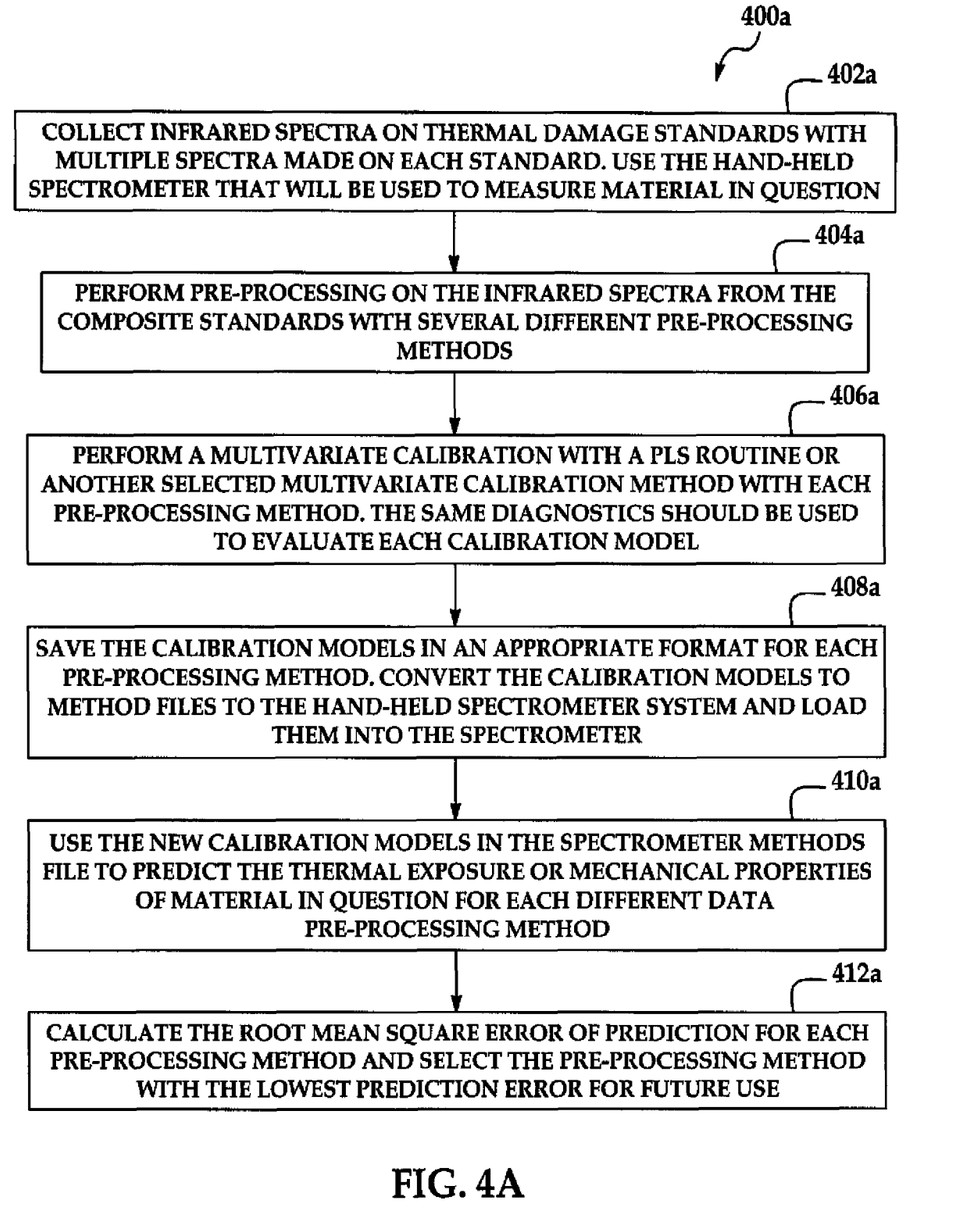
FIG. 4A is a flow diagram which illustrates important points in the multivariate calibration method.

Referring next to FIG. 4A, a flow diagram 400a which illustrates an illustrative embodiment of a method of optimizing the data pre-processing method for CFRP thermal effect calibration with multivariate methods is shown. In block 402a, a thermal effect standard is provided. The thermal effect standard may have been fabricated according to the method which was heretofore described with respect to the flow diagram 400 in FIG. 4. Infrared spectra on the thermal effect standards are collected, with multiple spectra obtained on each standard. A hand-held spectrometer which will be used to measure the material in question may be used. In block 404a, the infrared spectra of the thermal effect standards are made using the mid-IR wavelength range of from about 2.5 µm to about 15 µm. Pre-processing on the infrared spectra from the composite standards may be made using several different pre-processing methods. In block 406a, a multivariate calibration with a PLS routine or other multivariate calibration method may be performed with each pre-processing method. The same diagnostics should be used to evaluate each calibration model. In block 408a, the calibration methods may be saved in an appropriate format for each pre-processing method. The calibration models may be converted to method files which are compatible with the hand-held spectrometer system, and then the method files loaded into the spectrometer. In some embodiments, block 406a and block 408a may be replaced by collecting a single set of Validation Spectra that can be calculated by each new iteration of the calibration method. Ideally, these Validation Spectra may be collected on samples that are not included in the calibration set. In block 410a, the new calibration models in the spectrometer methods file may be used to predict the thermal exposure or mechanical properties of the material in question for each different data pre-processing method. In block 412a, the root mean square error of prediction for each pre-processing method is calculated. The pre-processing method having the lowest prediction error may be selected for future use. FIG. 3 illustrates the regression vector from the multivariate calibration of the mid-IR spectra to the un-notched compression test stress results of the standards using the PLS (partial least squares) multivariate calibration method.

Figure 5:
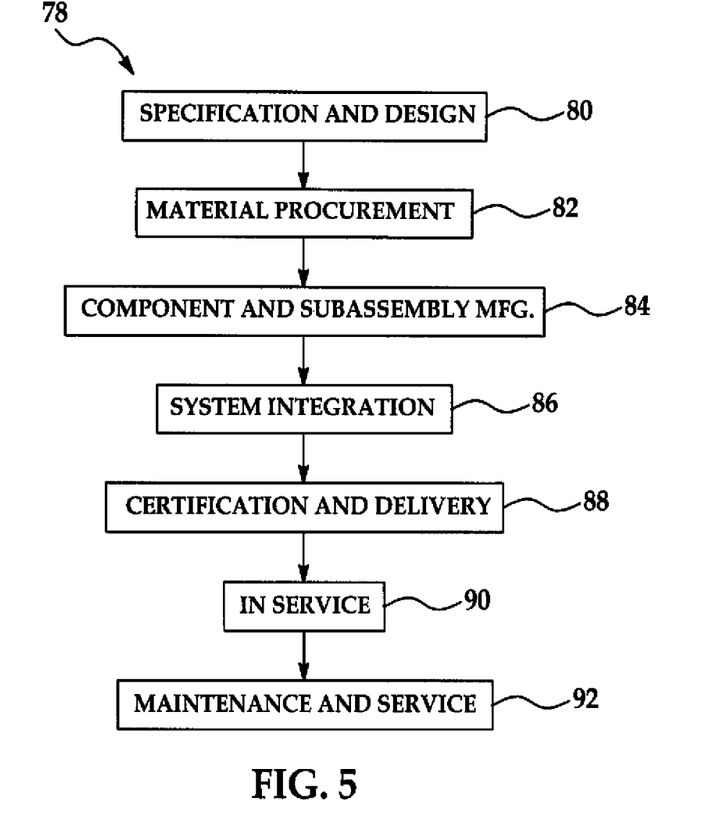
FIG. 5 is a flow diagram of an aircraft production and service methodology.
Figure 6:
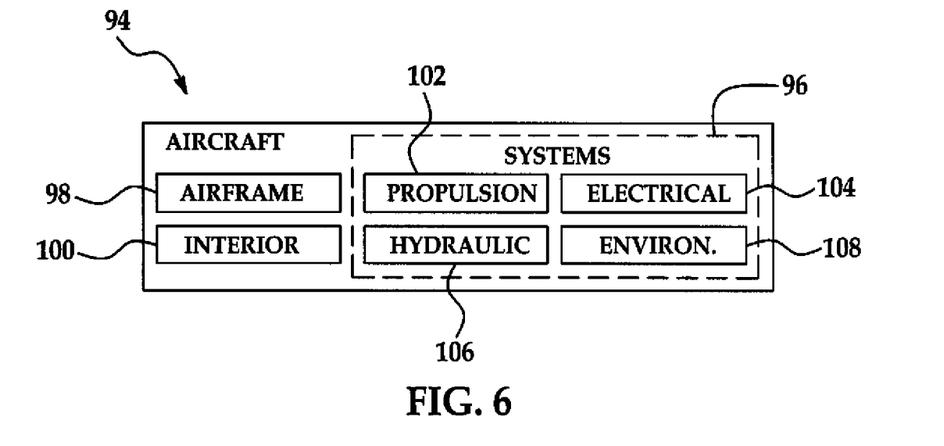
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the disclosure may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Referring next to FIGS. 7-10, an illustrative embodiment of a method for accurately assessing thermal effect in a coated or painted composite material using infrared spectroscopy, hereinafter method, is shown. While the methods herein are described with respect to assessing thermal effect in a coated or painted composite material, the method is equally suitable to assessing chemical effect in a coated or painted composite material. The method may utilize a spectrometer having a diffuse-reflectance sampling interface which is not affected by changes in surface reflectivity of paints and coatings. Generally, the method may utilize the coating or paint on a composite material as an indicator of the thermal history of the material. The method may eliminate the laborious process of having to remove the coating or paint layer prior to analyzing the underlying composite material. Consequently, thermal effect analysis time may be decreased and the need to expose the composite material to harsh chemicals and abrasive processes may be eliminated.

The method may include generating a calibration model by correlating infrared data to thermal effect information on painted or coated composite standards. A painted or coated composite material the thermal history of which is to be measured may then be provided. The painted or coated surface on the composite material may then be irradiated with infrared energy. The infrared energy which is reflected from the painted or coated surface on the composite material may be detected. A spectrum of the infrared energy which is reflected from the painted or coated surface on the composite material may be obtained. The thermal history of the painted or coated surface on an independently exposed composite material may be predicted using the calibration model.

Figure 7:
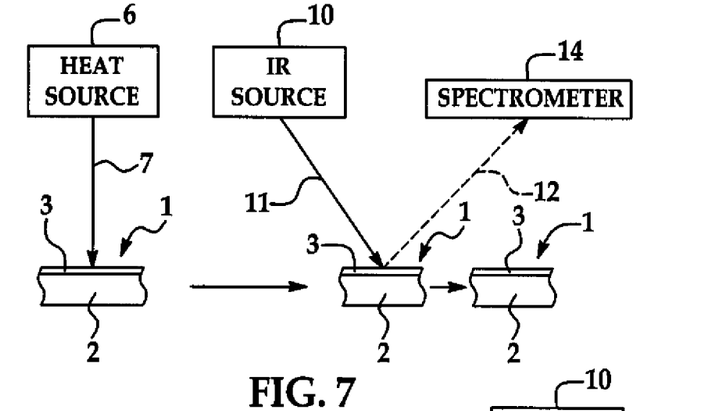
FIG. 7 is a block diagram which illustrates exemplary formulation of a calibration model in implementation of an illustrative embodiment of a method of predicting thermal or chemical effect in a painted or coated composite material.

An illustrative technique for defining a calibration model which is suitable for implementation of an illustrative embodiment of the method is shown in FIG. 7. Each of multiple composite standards 1 may include a composite substrate 2. A layer 3 may be provided on at least one surface of the composite substrate 2. In some applications, the layer 3 may include at least one paint layer. In some applications, the layer 3 may include at least one non-paint coating.

The layers 3 on the multiple composite standards 1 may be subjected to heat 7 which emanates from a heat source 6. The heat 7 which is applied to the layers 3 of the composite standards 1 may have various intensities. The layer 3 on each heat-treated composite standard 1 may then be irradiated with an infrared energy incident beam 11 which is emitted from an infrared source 10. In some applications, the infrared energy incident beam 11 may be mid-infrared energy. A reflected infrared beam 12 may be reflected from the layer 3 of each composite standard 1. The reflected infrared beams 12 may be received by a spectrometer 14, which may store infrared spectra (not shown) that correspond to the reflected infrared energy beams 12. In some applications, the spectrometer 14 may be a hand-held spectrometer. The infrared spectrum of each reflected infrared beam 12 may correspond to the thermal history of the layer 3 on the corresponding heat-treated composite standard 1.

In some embodiments, the IR source 10 and the spectrometer 14 may be a hand-held Exoscan infrared spectrometer having a diffuse-reflectance sampling interface, each of which may be obtained from A2 Technologies of Danbury, Conn. The Exoscan diffuse reflectance sampling interface is designed to bring the infrared energy incident beam 11 to the layer 3 on the substrate 2 at near normal incidence. The scattered light of the reflected infrared beam 12 is collected around the outside of the illumination cone. This may result in a more efficient collection mechanism for scattered light and may greatly reduce the amount of external reflectance observed (which results in negative spectral bands if the sample measured is reflective or semi-reflective).

Figure 8:
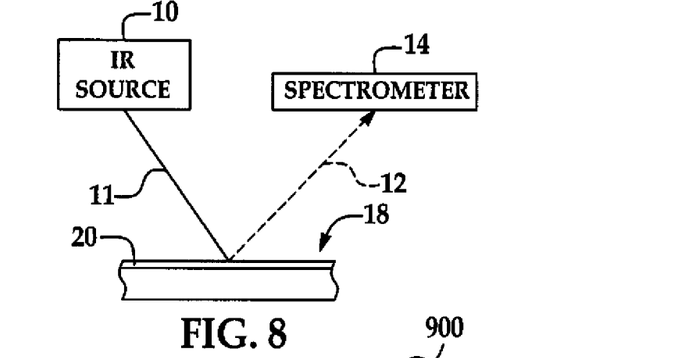
FIG. 8 is a block diagram which illustrates irradiation of a painted or coated composite part in implementation of an illustrative embodiment of a method of predicting thermal or chemical effect in a painted or coated composite material.

An illustrative technique for determining the thermal history of a composite material having a paint or coating which is suitable for implementation of an illustrative embodiment of the method is shown in FIG. 8. A composite material 18 the thermal history of which is to be measured may include a composite substrate 19. A coating layer 20 may be provided on the composite substrate 19. In some applications, the coating layer 20 may include at least one paint layer. In some applications, the coating layer 20 may include at least one non-paint coating.

The coating layer 20 on the composite substrate 19 of the composite material 18 may have been subjected to an unknown quantity of heat during normal use of the composite material 18. Accordingly, the thermal history of the coating layer 20, or the extent to which the coating layer 20 has been subjected to heat, may be measured by irradiating the coating layer 20 with an infrared energy incident beam 11 which is emitted from an infrared source 10. In some applications, the infrared energy incident beam 11 may be mid-infrared energy. A reflected infrared beam 12 may be reflected from the coating layer 20 of the composite material 18. The reflected infrared beam 12 may be received by a spectrometer 14, which may store an infrared spectrum (not shown) which corresponds to the reflected infrared energy beam 12. In some applications, the spectrometer 14 may be a hand-held spectrometer. The infrared spectrum of the reflected infrared energy beam 12 may correspond to the thermal history of the coating layer 20 on the heat-treated composite material 18.

Next, the calibration model may be defined by comparing the infrared spectrum of the infrared energy beam which was reflected from the coating layer 20 of the composite material 18 to the infrared spectra which were previously obtained for the composite standards 1 (FIG. 7). A match may be made between one of the infrared spectra of the calibration model and the infrared spectrum which was obtained from the composite material 18. Accordingly, the spectrum correlates to the thermal effect/chemical property via the calibration.

Figure 9:
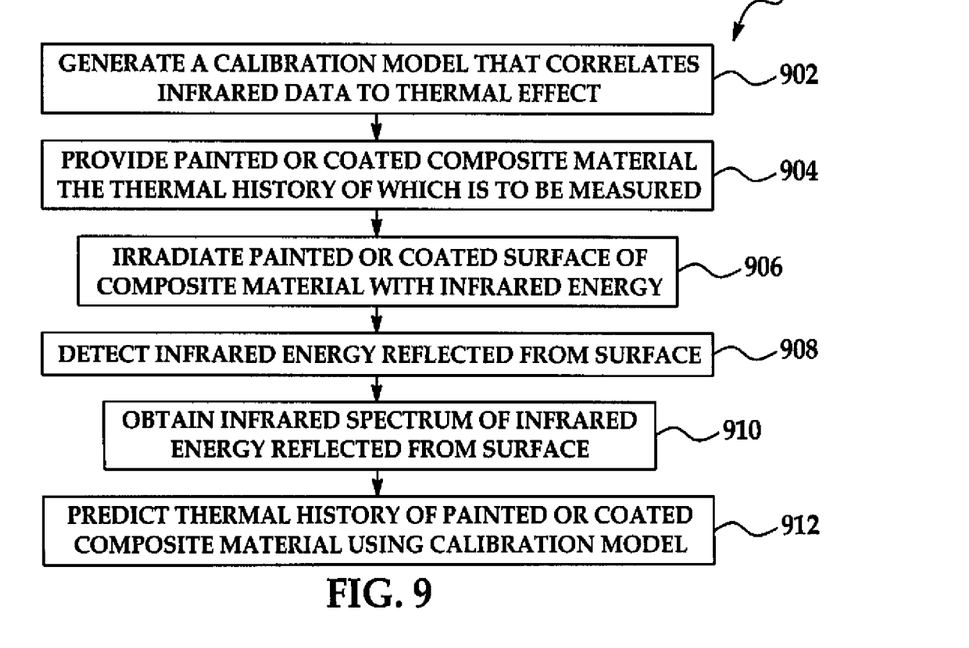
FIG. 9 is a flow diagram of an illustrative embodiment of a method of predicting thermal or chemical effect in a painted or composite material.

A flow diagram 900 of an illustrative embodiment of a method of predicting thermal effect in a painted or composite material is shown in FIG. 9. In block 902, a calibration model that correlates infrared data to thermal effect may be generated by correlating infrared data to thermal effect information on painted or coated composite standards. In block 904, a painted or coated composite material the thermal history of which is to be measured is provided. In block 906, the painted or coated surface of the composite material is irradiated with infrared energy. In block 908, infrared energy which is reflected from the painted or coated surface of the composite material is detected. In block 910, an infrared spectrum of the infrared energy reflected from the painted or coated surface of the composite material may be obtained. In block 912, the thermal history of the painted or coated composite material is predicted using the calibration model which was defined in block 902 and the infrared spectrum which was obtained in block 910.

Figure 10:
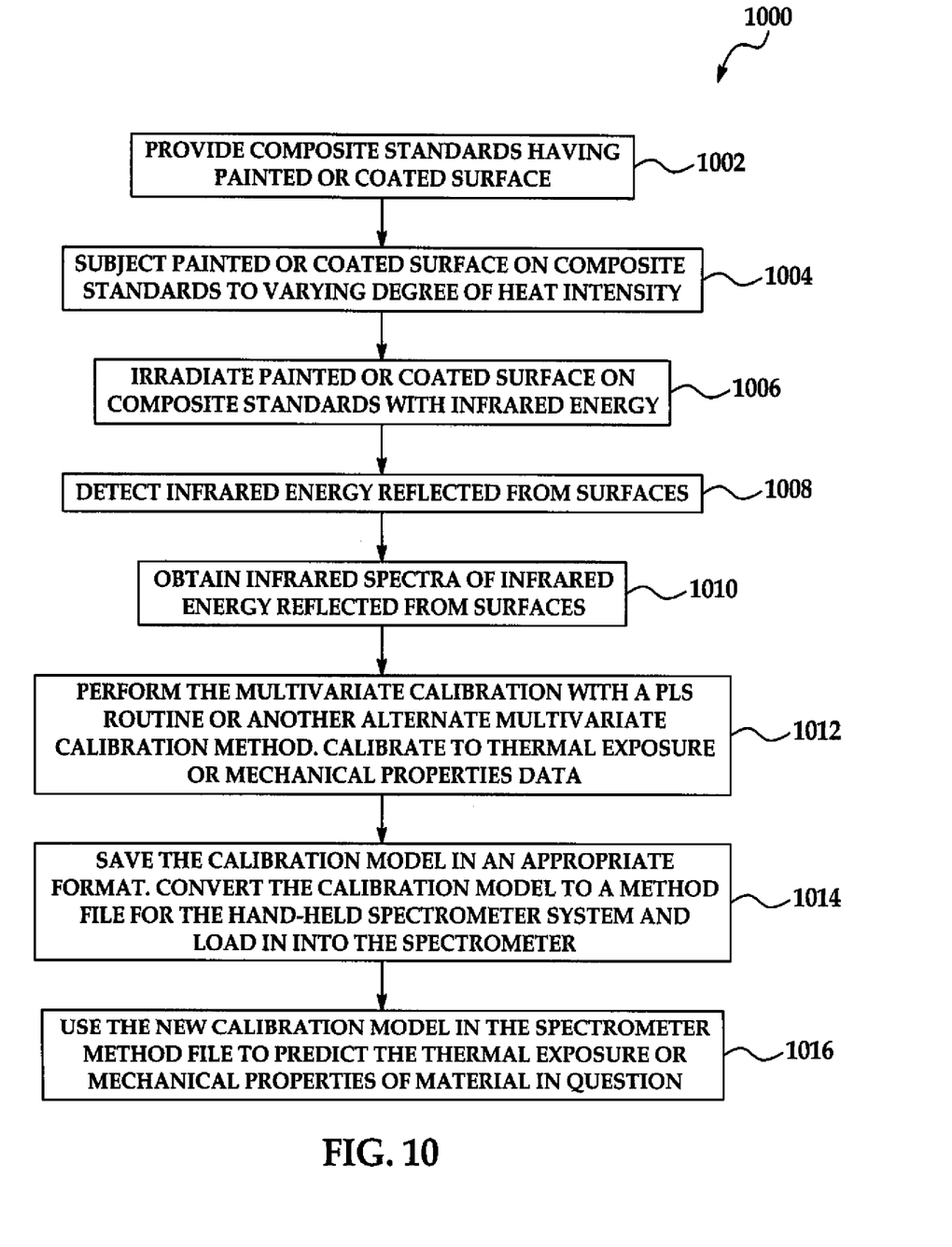
FIG. 10 is a flow diagram of an exemplary method of formulating a calibration model which is suitable for implementation of an illustrative embodiment of a method of predicting thermal or chemical effect in a painted or coated composite material.

A flow diagram 1000 of an exemplary method of formulating a calibration model which is suitable for implementation of an illustrative embodiment of a method of predicting thermal effect in a painted or coated composite material is shown in FIG. 10. In block 1002, composite standards each having a painted or coated surface are provided. In block 1004, the painted or coated surfaces on the composite standards are subjected to varying degrees of heat intensity. In block 1006, the painted or coated surfaces on the composite standards are irradiated with infrared energy. In block 1008, the infrared energy which is reflected from the painted or coated surfaces of the composite standards is detected. In block 1010, infrared spectra of infrared energy reflected from the surfaces may be obtained. In block 1012, the multivariate calibration may be performed using a PLS routine or another alternate multivariate calibration method. A calibration to thermal exposure or mechanical properties data may be made. In block 1014, the calibration model may be saved in an appropriate format. The calibration model may be converted to a method file for the hand-held spectrometer system and loaded into the spectrometer. In some embodiments, block 1012 and block 1014 may be replaced by collecting a single set of Validation Spectra that can be calculated by each new iteration of the calibration method. Ideally, these Validation Spectra may be collected on samples that are not included in the calibration set. In block 1016, the new calibration model in the spectrometer method file may be used to predict the thermal exposure or mechanical properties of the material in question.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of predicting thermal or chemical effect in a painted or coated composite material, comprising:
   generating a calibration model;
   providing a composite material having a coating layer;
   irradiating said coating layer with infrared energy;
   detecting infrared energy reflected from said coating layer; and
   predicting a thermal or chemical history of said coating layer using said calibration model and said infrared energy reflected from said coating layer.

2. The method of claim 1 wherein said providing a composite material having a coating layer comprises providing a composite material having at least one paint layer.

3. The method of claim 1 wherein said providing a composite material having a coating layer comprises providing a composite material having at least one non-paint coating.

4. The method of claim 1 wherein said irradiating said coating layer with infrared energy comprises irradiating said coating layer with mid-infrared energy.

5. The method of claim 1 wherein said detecting infrared energy reflected from said coating layer comprises obtaining an infrared spectrum of said infrared energy reflected from said coating layer.

6. The method of claim 1 wherein said irradiating said coating layer with infrared energy and detecting infrared energy reflected from said coating layer comprises providing a spectrometer and irradiating said coating layer with infrared energy and detecting infrared energy reflected from said coating layer using said spectrometer.

7. The method of claim 6 wherein said providing a spectrometer comprises providing a hand-held spectrometer.

8. The method of claim 7 wherein said providing a hand-held spectrometer comprises providing a hand-held spectrometer having a diffuse-reflectance sampling interface.

9. A method of predicting thermal or chemical effect in a painted or coated composite material, comprising:
- generating a calibration model by calibrating infrared data to thermal or chemical effect information on painted or coated composite standards;
- providing a composite material having a coating layer;
- irradiating said coating layer with infrared energy;
- detecting infrared energy reflected from said coating layer; and
- predicting a thermal or chemical history of said coating layer using said calibration model and said infrared energy reflected from said coating layer.

10. The method of claim 9 wherein said providing a composite material having a coating layer comprises providing a composite material having at least one paint layer.

11. The method of claim 9 wherein said providing a composite material having a coating layer comprises providing a composite material having at least one non-paint coating.

12. The method of claim 9 wherein said irradiating said coating layer with infrared energy comprises irradiating said coating layer with mid-infrared energy.

13. The method of claim 9 wherein said detecting infrared energy reflected from said coating layer comprises obtaining an infrared spectrum of said infrared energy reflected from said coating layer.

14. The method of claim 9 wherein said irradiating said coating layer with infrared energy and detecting infrared energy reflected from said coating layer comprises providing a spectrometer and irradiating said coating layer with infrared energy and detecting infrared energy reflected from said coating layer using said spectrometer.

15. The method of claim 14 wherein said providing a spectrometer comprises providing a hand-held spectrometer.

16. The method of claim 15 wherein said providing a hand-held spectrometer comprises providing a hand-held spectrometer having a diffuse-reflectance sampling interface.

17. A method of predicting thermal or chemical effect in a painted or coated composite material, comprising:
- generating a calibration model by calibrating infrared data to thermal effect information on painted or coated composite standards;
- providing a composite material having a coating layer;
- irradiating said coating layer with mid-infrared energy;
- detecting infrared energy reflected from said coating layer;
- obtaining an infrared spectrum of said infrared energy reflected from said coating layer; and
- predicting a thermal or chemical history of said coating layer using said calibration model and said infrared energy reflected from said coating layer.

18. The method of claim 17 wherein said irradiating said coating layer with infrared energy and detecting infrared energy reflected from said coating layer comprises providing a spectrometer and irradiating said coating layer with infrared energy and detecting infrared energy reflected from said coating layer using said spectrometer.

19. The method of claim 18 wherein said providing a spectrometer comprises providing a hand-held spectrometer.

20. The method of claim 19 wherein said providing a hand-held spectrometer comprises providing a hand-held spectrometer having a diffuse-reflectance sampling interface.

21. A method of predicting thermal effect in a painted or coated composite material, comprising:
- generating a calibration model by providing composite standards having painted or coated surfaces, subjecting said painted or coated surfaces on said composite standards to varying degrees of heat intensity, irradiating said painted or coated surfaces on said composite standards with infrared energy, detecting said infrared energy reflected from said surfaces and obtaining infrared spectra of said infrared energy reflected from said surfaces;
- providing a composite material having a painted or coated layer;
- providing a hand-held spectrometer having a diffuse-reflectance sampling interface;
- irradiating said layer with mid-infrared energy from said spectrometer;
- detecting infrared energy reflected from said painted or coated layer with said spectrometer;
- obtaining an infrared spectrum of said infrared energy reflected from said painted or coated layer; and
- predicting a thermal history of said painted or coated layer using said calibration model and said infrared energy reflected from said painted or coated layer.

* * * * *